(12) United States Patent
Saint-Remy

(10) Patent No.: US 11,236,127 B2
(45) Date of Patent: Feb. 1, 2022

(54) MODULATION OF ANTIGEN IMMUNOGENICITY BY ADDITION OF EPITOPES RECOGNIZED BY NKT CELLS

(75) Inventor: Jean-Marie Saint-Remy, Grez-Doiceau (BE)

(73) Assignee: Imnate Sarl, Strassen (LU)

( * ) Notice: Subject to any disclaimer, the term of this patent is extended or adjusted under 35 U.S.C. 154(b) by 1335 days.

(21) Appl. No.: 13/989,351

(22) PCT Filed: Nov. 24, 2011

(86) PCT No.: PCT/EP2011/070907
§ 371 (c)(1),
(2), (4) Date: Jun. 25, 2013

(87) PCT Pub. No.: WO2012/069572
PCT Pub. Date: May 31, 2012

(65) Prior Publication Data
US 2013/0302375 A1    Nov. 14, 2013

(30) Foreign Application Priority Data
Nov. 25, 2010  (EP) .................................... 10192564

(51) Int. Cl.
| | |
|---|---|
| *A61K 39/00* | (2006.01) |
| *A61K 39/04* | (2006.01) |
| *A61K 39/12* | (2006.01) |
| *C07K 2/00* | (2006.01) |
| *A61K 39/35* | (2006.01) |
| *A61K 39/145* | (2006.01) |
| *A61K 39/39* | (2006.01) |
| *C07K 14/435* | (2006.01) |

(52) U.S. Cl.
CPC ............ *C07K 2/00* (2013.01); *A61K 39/0011* (2013.01); *A61K 39/04* (2013.01); *A61K 39/12* (2013.01); *A61K 39/145* (2013.01); *A61K 39/35* (2013.01); *A61K 39/39* (2013.01); *C07K 14/43531* (2013.01); *A61K 2039/55505* (2013.01); *A61K 2039/57* (2013.01); *C12N 2760/16034* (2013.01); *Y02A 50/30* (2018.01)

(58) Field of Classification Search
None
See application file for complete search history.

(56) References Cited

FOREIGN PATENT DOCUMENTS

| | | |
|---|---|---|
| WO | WO 02/19968 A2 | 3/2002 |
| WO | WO 2010/037395 A2 | 4/2010 |
| WO | WO 2010/037402 A1 | 4/2010 |
| WO | WO 2010/065544 A2 | 6/2010 |

OTHER PUBLICATIONS

Girardi et al. (JBC, 2016, 291 (20): 10677-10683).*
Terabe and Berzofsky (Adv. Canc. Res. 2008, 101: 277-348).*
Horst et al (Viruses, 2012, 4: 2379-2399) (Year: 2012).*
Brutkiewicz et al (Curr. Opin. Immunol., 2018, 52: 87-92) (Year: 2018).*
Arrenberg et al., "Oligoclonality and innate-like features in the TCR repertoire of type II NKT cells reactive to a beta-linked self-glycolipid," *Proceedings of the National Academy Of Sciences USA*, vol. 107, No. 24, pp. 10984-10989 (2010).
Brutkiewicz, *Journal of Immunology*, vol. 177, pp. 769-775 (2006).
Burrows et al., *Nature Immunology*, vol. 10, No. 7, pp. 669-671 (2009).
Castano et al., "Peptide Binding and Presentation by Mouse CD1," *Science*, vol. 269, No. 5221, pp. 223-226 (1995).
Godfrey et al., "Raising the NKT cell family," *Nature Immunology*, vol. 11, No. 3, pp. 197-206 (2010).
Lee et al., "Induction of an Antigen-specific, CD 1-restricted Cytotoxic T Lymphocyte Response In vivo," *Journal of Experimental Medicine*, vol. 187, No. 3, pp. 433-438 (1998).
Matsuda et al., "CD1d-restricted iNKT cells, the 'Swiss-Army knife' of the immune system," *Current Opinion in Immunology*, vol. 20, No. 3, pp. 358-368 (2008).
Schnolzer et al., "In situ neutralization in Boc-chemistry solid phase peptide synthesis. Rapid, high yield assembly of difficult sequences.," *Int. J Pept. Protein Res.*, vol. 40, pp. 180-193 (1992)—ABSTRACT.
Scott et al., "Dendritic Cells Permit Identification of Genes Encoding MHC Class II-Restricted Epitopes of Transplantation Antigens," *Immunity*, vol. 12, pp. 711-720, (2000).
Tam et al., "Methods and Strategies of Peptide Ligation," *Biopolymers*, vol. 60, pp. 194-205 (2001).
Tangri et al., "Presentation of Peptide Antigens by Mouse CD1 Requires Endosomal Localization and Protein Antigen Processing," *Proceedings of the National Academy of Sciences USA*, vol. 95, No. 24, pp. 14314-14319 (1998).
Texier et al., "HLA-DR Restricted Peptide Candidates for Bee Venom Immunotherapy," *The Journal of Immunology*, vol. 164, No. 6, pp. 3177-3184 (2000).
European Patent Office, International Search Report in International Application No. PCT/EP2011/070907 (dated Feb. 28, 2012).

\* cited by examiner

*Primary Examiner* — Michael Szperka
*Assistant Examiner* — Marianne DiBrino
(74) *Attorney, Agent, or Firm* — Leydig, Voit & Mayer, Ltd.

(57) ABSTRACT

The invention describes a method and compounds for the prevention and treatment of infections with intracellular organisms, the treatment of tumors, and the prevention of infectious and allergic diseases by vaccination.

8 Claims, No Drawings

Specification includes a Sequence Listing.

SEQUENCE LISTING

```
<160> NUMBER OF SEQ ID NOS: 11

<210> SEQ ID NO 1
<211> LENGTH: 95
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 2
<211> LENGTH: 95
<212> TYPE: PRT
<213> ORGANISM: Mycobacterium tuberculosis

<400> SEQUENCE: 2

Met Thr Glu Gln Gln Trp Asn Phe Ala Gly Ile Glu Ala Phe Ala Ser
1               5                   10                  15

Ala Ile Gln Phe Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45
```

```
Glu Ala Tyr Gln Gly Val Gln Gln Lys Trp Asp Ala Thr Ala Thr Glu
         50                  55                  60

Leu Asn Asn Ala Leu Gln Asn Leu Ala Arg Thr Ile Ser Glu Ala Gly
 65                  70                  75                  80

Gln Ala Met Ala Ser Thr Glu Gly Asn Val Thr Gly Met Phe Ala
                 85                  90                  95
```

<210> SEQ ID NO 3
<211> LENGTH: 386
<212> TYPE: PRT
<213> ORGANISM: Gallus sp.

<400> SEQUENCE: 3

```
Met Gly Ser Ile Gly Ala Ala Ser Met Glu Phe Cys Phe Asp Val Phe
 1               5                  10                  15

Lys Glu Leu Lys Val His His Ala Asn Glu Asn Ile Phe Tyr Cys Pro
                 20                  25                  30

Ile Ala Ile Met Ser Ala Leu Ala Met Val Tyr Leu Gly Ala Lys Asp
             35                  40                  45

Ser Thr Arg Thr Gln Ile Asn Lys Val Val Arg Phe Asp Lys Leu Pro
 50                  55                  60

Gly Phe Gly Asp Ser Ile Glu Ala Gln Cys Gly Thr Ser Val Asn Val
 65                  70                  75                  80

His Ser Ser Leu Arg Asp Ile Leu Asn Gln Ile Thr Lys Pro Asn Asp
                 85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Thr Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
```

```
                        325                 330                 335
Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
                355                 360                 365

Ile Lys His Ile Ala Thr Asn Ala Val Leu Phe Phe Gly Arg Cys Val
            370                 375                 380

Ser Pro
385

<210> SEQ ID NO 4
<211> LENGTH: 386
<212> TYPE: PRT
<213> ORGANISM: Gallus sp.

<400> SEQUENCE: 4

Met Gly Ser Ile Gly Ala Ala Ser Met Glu Phe Cys Phe Asp Val Phe
1               5                   10                  15

Lys Glu Leu Lys Val Phe His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Phe Thr Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300
```

```
Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
            325                 330                 335

Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
            370                 375                 380

Ser Pro
385

<210> SEQ ID NO 5
<211> LENGTH: 565
<212> TYPE: PRT
<213> ORGANISM: Influenza A virus

<400> SEQUENCE: 5

Met Lys Ala Lys Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Leu Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ala Cys Tyr Pro Gly Asp Phe
            100                 105                 110

Ile Asp Tyr Glu Glu Leu Lys Glu Gln Leu Ser Ser Val Ser Ser Leu
        115                 120                 125

Glu Arg Phe Glu Ile Phe Pro Lys Glu Ser Ser Trp Pro Asn His Asn
    130                 135                 140

Thr Lys Gly Val Thr Ala Ser Cys Ser His Gly Gly Lys Ser Ser Phe
145                 150                 155                 160

Tyr Arg Asn Leu Leu Trp Leu Thr Lys Thr Glu Asp Ser Tyr Pro Lys
                165                 170                 175

Leu Ser Asn Ser Tyr Val Asn Asn Lys Gly Lys Glu Val Leu Val Leu
            180                 185                 190

Trp Gly Val His His Pro Ser Ser Asp Glu Gln Gln Ser Leu Tyr
        195                 200                 205

His Asn Val Asn Ala Tyr Val Ser Val Val Ser Ser Asn Tyr Asn Gly
    210                 215                 220

Arg Phe Thr Pro Glu Ile Ala Ala Arg Pro Lys Val Arg Asn Gln His
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Gly Ser Gly Ile Ile Thr Ser Asn Ala Ser Met
        275                 280                 285
```

His Glu Cys Asn Thr Lys Cys Gln Thr Pro Gln Gly Ala Ile Asn Ser
            290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Phe Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Ser Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Leu Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Lys Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 6
<211> LENGTH: 565
<212> TYPE: PRT
<213> ORGANISM: Influenza A virus

<400> SEQUENCE: 6

Met Lys Ala Lys Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Leu Leu Glu Lys Asn Val

```
            85                  90                  95
Val Glu Thr Pro Asn Ser Glu Asn Gly Ala Cys Tyr Pro Gly Asp Phe
            100                 105                 110
Ile Asp Tyr Glu Glu Leu Lys Glu Gln Leu Ser Ser Val Ser Ser Leu
            115                 120                 125
Glu Arg Phe Glu Ile Phe Pro Lys Glu Ser Ser Trp Pro Asn His Asn
            130                 135                 140
Thr Lys Gly Val Thr Ala Ser Cys Ser His Gly Gly Lys Ser Ser Phe
145                 150                 155                 160
Tyr Arg Asn Leu Leu Trp Leu Thr Lys Thr Glu Asp Ser Tyr Pro Lys
                165                 170                 175
Leu Ser Asn Ser Tyr Val Asn Asn Lys Gly Lys Glu Val Leu Val Leu
                180                 185                 190
Trp Gly Val His His Pro Ser Ser Asp Glu Gln Gln Ser Leu Tyr
                195                 200                 205
His Asn Val Asn Ala Tyr Val Ser Val Val Ser Ser Asn Tyr Asn Gly
            210                 215                 220
Arg Phe Thr Pro Glu Ile Ala Ala Arg Pro Lys Val Arg Asn Gln His
225                 230                 235                 240
Gly Arg Met Asn Tyr Tyr Trp Thr Leu Leu Glu Pro Gly Asp Thr Ile
                245                 250                 255
Ile Phe Glu Ala Thr Gly Asn Leu Ile Ala Pro Trp Tyr Ala Phe Ala
            260                 265                 270
Leu Ser Arg Gly Phe Gly Ser Gly Ile Ile Thr Ser Asn Ala Ser Met
            275                 280                 285
His Glu Cys Asn Thr Lys Cys Gln Thr Pro Gln Gly Ala Ile Asn Ser
            290                 295                 300
Ser Leu Pro Phe Gln Asn Ile His Pro Phe Thr Ile Gly Glu Cys Pro
305                 310                 315                 320
Lys Tyr Val Arg Ser Thr Lys Leu Arg Met Val Thr Gly Leu Arg Asn
                325                 330                 335
Ile Pro Ser Ile Gln Phe Arg Gly Leu Phe Gly Phe Ile Ala Gly Phe
            340                 345                 350
Ile Glu Gly Gly Trp Thr Gly Met Ile Asp Gly Trp Tyr Gly Tyr His
            355                 360                 365
His Gln Asn Glu Gln Gly Ser Gly Tyr Ala Ala Asp Gln Lys Ser Thr
            370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Ser Lys Glu Phe Asn Asn Leu
                405                 410                 415
Glu Lys Arg Met Glu Asn Leu Asn Lys Lys Val Asp Asp Gly Phe Leu
                420                 425                 430
Asp Ile Trp Thr Tyr Asn Ala Glu Leu Leu Val Leu Leu Glu Asn Glu
            435                 440                 445
Arg Thr Leu Asp Phe His Asp Leu Asn Val Phe Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asp Asn Lys Cys Met Glu Ser Val Arg
                485                 490                 495
Asn Gly Thr Tyr Asp Tyr Pro Lys Tyr Ser Glu Glu Ser Lys Leu Asn
            500                 505                 510
```

```
Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 7
<211> LENGTH: 129
<212> TYPE: PRT
<213> ORGANISM: Dermatophagoides pteronyssinus

<400> SEQUENCE: 7

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Ala Lys Val Met Gly
            100                 105                 110

Asp Asp Gly Val Leu Ala Cys Ala Ile Ala Thr His Ala Lys Ile Arg
        115                 120                 125

Asp

<210> SEQ ID NO 8
<211> LENGTH: 136
<212> TYPE: PRT
<213> ORGANISM: Dermatophagoides pteronyssinus

<400> SEQUENCE: 8

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Ala Lys Val Met Gly
            100                 105                 110

Asp Asp Gly Val Leu Ala Cys Ala Ile Ala Thr His Ala Lys Ile Arg
        115                 120                 125
```

Asp Phe Ala Ala Leu Ala Ala Phe
    130                 135

<210> SEQ ID NO 9
<211> LENGTH: 7
<212> TYPE: PRT
<213> ORGANISM: artificial sequence
<220> FEATURE:
<223> OTHER INFORMATION: Peptides from EG7 tumor cells

<400> SEQUENCE: 9

Phe Lys Glu Leu Lys Val His
1               5

<210> SEQ ID NO 10
<211> LENGTH: 7
<212> TYPE: PRT
<213> ORGANISM: artificial sequence
<220> FEATURE:
<223> OTHER INFORMATION: Peptide from EG7 tumor cell

<400> SEQUENCE: 10

Phe Lys Gly Leu Trp Glu Lys
1               5

<210> SEQ ID NO 11
<211> LENGTH: 7
<212> TYPE: PRT
<213> ORGANISM: artificial sequence
<220> FEATURE:
<223> OTHER INFORMATION: allergen from house dust mite

<400> SEQUENCE: 11

Phe Ala Ala Leu Ala Ala Phe
1               5

MODULATION OF ANTIGEN IMMUNOGENICITY BY ADDITION OF EPITOPES RECOGNIZED BY NKT CELLS

CROSS-REFERENCE TO RELATED APPLICATIONS

This patent application is the U.S. national phase of International Application No. PCT/EP2011/070907, filed on Nov. 24, 2011, which claims the benefit of European Patent Application No. 10192564.2, filed Nov. 25, 2010, the disclosures of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 021,532 Byte ASCII (Text) file named "5510803REV1 ST25," created on Aug. 19, 2016.

FIELD OF THE INVENTION

The present invention relates to peptides or polypeptides with capacity to recruit and activate NKT cells and their use in treating infections with intracellular organisms or tumors, and preventing diseases by vaccination strategies.

BACKGROUND OF THE INVENTION

Chronic infectious diseases due to intracellular pathogens are difficult to treat because infected cells reduce surface expression of a number of molecules which would normally allow the immune system to specifically recognize said infected cells. Examples are *Mycobacterium* infections in which infected cells inhibit expression of molecules of the major histocompatibility (MHC) complexes thereby preventing recognition by T lymphocytes of the CD8 lineage (via MHC class I recognition) and by lymphocytes of the CD4 lineage (via class II MHC recognition). In fact, many bacteria and viruses have elaborated methods to escape recognition of infected cells.

To some extent, the same mechanisms allow tumors to escape detection. A few of such tumors express MHC class II determinants at least under inflammatory conditions. Recent experiments have shown that even when increased CD8 recognition of MHC class I-presented tumor derived peptides by for instance vaccination, the overall effect on tumor growth remains limited.

Both in chronic infection with intracellular pathogens and in tumors, there is an urgent need to elaborate new methods by which infected, or tumor cells, respectively, would be recognized and eliminated.

Vaccination for infectious diseases is current practice. Yet, in a significant number of conditions, the efficacy of vaccination is limited by the preferential induction of specific antibodies to the pathogens and no or little elicitation of immune cells which would recognize infected cells. Thus, prevention of viral and bacterial diseases by vaccination is often of limited efficacy. Examples are to be found in the efficacy of several vaccines for viral diseases, such as influenza virus, rotavirus or even poliovirus at least in some world areas. In some instances, the antigens considered for vaccination are weak immunogens and, due to the large diversity of MHC determinants, a significant variation in efficacy is observed from one subject to the other.

Vaccination for allergic diseases also suffers from limitations related to either the weak immunogenicity of allergens or to the lack of control of risks related to the administration of an allergen to a subject precisely prone to react with allergic symptoms.

In both vaccinations against infectious agents and against allergens there is a need for more efficient and more secure methods.

Natural killer T (NKT) cells constitute a distinct lineage of non-conventional T lymphocytes that recognize antigens presented by the non-classical MHC complex molecule CD1d. Two subsets of NKT cells are presently described. Type 1 NKT cells, also called invariant NKT cells (iNKT), are the most abundant. They are characterized by the presence of an alpha-beta T cell receptor (TCR) made of an invariant alpha chain, Valpha14 in the mouse and Valpha24 in humans. This alpha chain is associated to a variable though limited number of beta chains. Type 2 NKT cells have an alpha-beta TCR but with a polymorphic alpha chain. However, it is apparent that other subsets of NKT cells exist, the phenotype of which is still incompletely defined, but which share the characteristics of being activated by glycolipids presented in the context of the CD1d molecule.

NKT cells typically express a combination of natural killer (NK) cell receptor, including NKG2D and NK1.1. NKT cells are part of the innate immune system, which can be distinguished from the adaptive immune system by the fact that they do not require expansion before acquiring full effector capacity. Activation of NKT cells results in various effects. Such cells release preformed mediators, including a large array of cytokines (including IL-4, IFN-gamma, IL-21 and IFN-alpha) which provide help to B cells for the production of antibodies and it has been suggested that the release of cytokines could also influence CD4+ T cells (Burrows et al Nature Immunology 2009, 10: 669-671). In the context of the present invention, increasing B cell activation and major histocompatibility (MHC) class II-restricted CD4+ T cells activation would be beneficial.

The recognition unit for NKT cells, the CD1d molecule, has a structure closely resembling that of the MHC class I molecule, including the presence of beta-2 microglobulin. It is characterized by a deep cleft bordered by two alpha chains and containing highly hydrophobic residues, which accepts lipid chains. The cleft is open at both extremities, allowing to accommodate longer chains. The canonical ligand for CD1d is the synthetic alpha galactosylceramide (alpha GalCer). However, many natural alternative ligands have been described, including glyco- and phospholipids, the natural lipid sulfatide found in myelin, microbial phosphoinositol mannoside and alpha-glucuronosylceramide. The present consensus (see reviews, such as Matsuda et al, Current Opinion in Immunology 2008, 20:358-368 and Godfrey et al, Nature reviews Immunology 2010, 11: 197-206) is that CD1d binds only ligands containing lipid chains, or in general a common structure made of a lipid tail which is buried into CD1d and a sugar residue head group that protrudes out of CD1d.

Peptides are not deemed to be able to activate NKT cells through presentation by CD1d. It was, however, suggested that long hydrophobic peptides containing bulky aminoacid residues could bind to CD1d (Castano et al, Science 1995, 269: 223-226). Observations carried out using phage display libraries expressing random sequence peptides with no defined physiological relevance, allowed establishing a theoretical consensus motif (Castano et al, Science 1995, 269: 223-226 and see below).

In fact, Castano et al show that the cells which are activated are CD8+ T cells, namely MHC class I restricted cells, and not NKT cells. These findings teach the one skilled in the art that there is no evidence that hydrophobic peptides are presented by CD1d molecules. The physiological relevance of the claims made by Castano et al was further questioned due to the inability to elicit NKT cells under conventional immunization protocols (Matsuda et al, Current Opinion in Immunology 2008, 20:358-368 and Brutkiewicz Journal of Immunology 2006, 177: 769-775). Artificial systems such as immunization with cells transfected to overexpress CD1d and loaded in vitro with an ovalbumin-derived peptide were able to elicit NKT cells. Likewise, intradermal immunization with plasmid DNA together with murine CD1d and costimulatory molecules induce cytolytic CD1d-restricted T cells (Lee et al, Journal of Experimental Medicine 1998, 187: 433-438). Hydrophobic peptides containing a structural motif made of an aromatic residue in position P1 and P7, and an aliphatic chain in position P4 were claimed by Castano et al (Science 269: 223, 1995) to contain a core motif for CD1d binding epitopes. As described above, the conclusions reached by Castano et al are not supported by data.

We made the unexpected finding that peptides encompassing a hydrophobic aminoacid sequence are in fact capable of eliciting activation of NKT cells.

Additionally, activation of NKT cells provides a way to increase the efficiency of vaccines against infectious diseases and against allergens, due to the large amounts of cytokines secreted by NKT cells which help in eliciting B cell and class II restricted T cell activation (Burrows et al Nature Immunology 2009, 10: 669-671) and thereby the production of antibodies.

If epitopes from proteins could bind to CD1d, then addition of a CD1d binding motif to a protein could increase activation of NKT cells, which could result in either induction of antigen-presenting cell killing, as it would be appropriate for the treatment of infections with intracellular pathogens or of tumors, or increase the immunogenicity of antigens, as would be appropriate in vaccination strategies for infectious diseases or allergy.

Examples of infection with intracellular pathogens include *Mycobacterium* infections, intracellular bacterial infection, viral diseases and parasitic infections. Examples of tumors are any tumor expressing CD1d. Examples of antigens used for vaccination are virus proteins used in influenza vaccination, oral rotavirus or oral poliovirus vaccination and allergen vaccination.

More specifically, addition of a CD1d-binding motif would be of use when it is desirable to increase the killing activity of NKT cells towards antigen-presenting cells, or to increase the production of cytokines made by NKT cells and thereby increase immunogenicity.

Generating new CD1d binding motif(s) within the natural sequence of peptides or polypeptides, or adding CD1d binding motif(s) to such peptides or polypeptides to recruit and activate NKT cells forms the basis of the present invention.

SUMMARY OF THE INVENTION

The present invention relates to the use of peptides or polypeptides for the treatment of infections with intracellular pathogens in a subject by increasing the elimination of cells carrying such pathogens.

The present invention also relates to the use of peptides or polypeptides for the therapy of tumors in a subject by increasing recognition and killing of tumor cells.

The present invention also relates to the use of peptides or polypeptides for vaccination purposes in a subject with antigens from infectious agents or allergens.

We made the unexpected observation that peptides can be presented by CD1d molecules and activate NKT cells. Activation of such cells results in acquisition of cytolytic properties against the cell presenting the peptide bound to CD1d and in the release of cytokines.

The present invention relates in one aspect to the use of at least one isolated immunogenic peptide or polypeptide derived from an intracellular pathogen, which is modified by generating at least one CD1d binding motif within the natural sequence of said peptide or polypeptide, or by adding at least one CD1d binding motif to said peptide or polypeptide as a medicament for treating in a subject infection with said intracellular pathogen.

The present invention also relates in one aspect to the use of at least one isolated immunogenic peptide or polypeptide derived from a tumor, which is modified by generating at least one new CD1d binding motif within the natural sequence of said peptide or polypeptide, or by adding at least one CD1d binding motif to said peptide or polypeptide as a medicament for treating in a subject said tumor.

The present invention also relates in one aspect to the use of at least one isolated immunogenic peptide or polypeptide derived from an extracellular infectious agent, which is modified by generating at least one new CD1d binding motif within the natural sequence of said peptide or polypeptide, or by adding at least one CD1d binding motif to said peptide or polypeptide as a medicament for preventing in a subject said infection.

The present invention also relates in one aspect to the use of at least one isolated immunogenic peptide or polypeptide derived from an allergen, which is modified by generating at least one new CD1d binding motif within the natural sequence of said peptide or polypeptide, or by adding at least one CD1d binding motif to said peptide or polypeptide as a medicament for preventing in a subject allergic reactions.

It should be clear for the one skilled in the art that the generation of a CD1d binding motif, in any of the indications listed above, implies that said motif, when presented by the CD1d molecule expressed by an antigen-presenting cell, is recognized by NKT cells and activate said NKT cells.

In a further aspect, the invention also covers the use of at least one isolated peptide or polypeptide derived from an intracellular pathogen, a tumor, an infectious agent or an allergen, which is modified by generating at least one new CD1d binding motif within the natural sequence of said peptide or polypeptide, or by adding at least one CD1d binding motif to said peptide or polypeptide to recruit and activate NKT cells, as a medicament for activating in a subject cytolytic activity and cytokine production by CD4+ NKT cells in said subject.

In any of the above uses said peptide or polypeptide derived from an intracellular pathogen may be any peptide or polypeptide derived from viruses, bacteria, mycobacteria or parasites with an intracellular life cycle. Viruses include ssDNA, dsDNA and RNA viruses, with as examples Herpesviridae, Flaviviridae and Picornaviridae, influenza, measles and immunodeficiency viruses. Bacteria and mycobacteria include *Mycobacterium tuberculosis*, other mycobacteria pathogenic for humans or animals, Yersiniosis, *Brucella*, Chlamydiae, *Mycoplasma*, Rickettsiae, Salmonellae and Shigellae. Parasites include Plasmodiums, Leishmanias, Trypanosomas, *Toxoplasma gondii, Listeria, Histoplasma*.

In any of the above uses said peptide or polypeptide derived from a tumor may be any peptide or polypeptide derived from: (1) oncogenes, such as the MAGE identified in some melanomas; (2) proto-oncogenes, such as cyclin D1 expressed on soft tissues carcinomas such as those of the kidney or parathyroid, as well as in multiple myeloma; (3) virus-derived proteins, such as those from the Epstein-Barr virus in some carcinomas and in some Hodgkin-type lymphomas; (4) surviving factors, which are anti-apoptotic factors such as survivin or bcl2; (5) clonotypic determinants, such as idiotypic determinants derived from B cell receptor in follicular lymphomas or multiple myelomas or T cell receptor determinants in T cell malignancies In any of the above uses said peptide or polypeptide derived from an infectious agent, including viruses, bacteria and parasites.

In any of the above uses said peptide or polypeptide derived from an allergen may be any peptide or polypeptide derived from
- food allergens present in peanuts, fish e.g. codfish, egg white, crustacea e.g. shrimp, milk e.g. cow's milk, wheat, cereals, fruits of the Rosacea family (apple, plum, strawberry), vegetables of the Liliacea, Cruciferae, Solanaceae and Umbelliferae families, tree nuts, sesame, peanut, soybean and other legume family allergens, spices, melon, avocado, mango, fig, banana, . . .
- house dust mites allergens obtained from *Dermatophagoides* spp or *D. pteronyssinus, D. farinae* and *D. microceras, Euroglyphus maynei* or *Blomia* sp.,
- allergens from insects present in cockroach or Hymenoptera,
- allergens from pollen, especially pollens of tree, grass and weed,
- allergens from animals, especially in cat, dog, horse and rodent,
- allergens from fungi, especially from *Aspergillus, Alternaria* or *Cladosporium*, and
- occupational allergens present in products such as latex or amylase.

The invention further encompasses isolated viral vectors characterized in that they comprise at least one peptide or polypeptide derived from an intracellular pathogen, from a tumor, from an infectious agent or from an allergen wherein at least one new CD1d binding motif is generated within the natural sequence of said peptide or polypeptide, or wherein at least one CD1d binding motif is added.

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification. The term "polypeptide" when used herein refers to generally longer peptides or proteins.

The term "epitope" when used herein refers to one or several portions (which may define a conformational epitope) of a protein which is/are specifically recognized and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

The term "allergen" refers to a specific subset of antigen characterized by its capacity to elicit antibodies of the IgE isotype in predisposed individuals.

The term "T cell epitope" or "T-cell epitope" in the context of the present invention refers to a dominant, sub-dominant or minor T cell epitope, i.e., a part of an antigenic protein that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules.

The term "NKT cell epitope" refers to a part of an antigenic protein that is specifically recognized and bound by a receptor at the cell surface of a T lymphocyte. In particular, a NKT cell epitope is an epitope bound by CD1d molecules.

The term "CD4+ effector cells" refers to cells belonging to the CD4-positive subset of T-cells whose function is to provide help to other cells, such as, for example B-cells. These effector cells are conventionally reported as Th cells (for T helper cells), with different subsets such as Th0, Th1, Th2, and Th17 cells.

The term "NKT cells" refers to cells of the innate immune system characterized by the fact that they carry receptors such as NK1.1 and NKG2D, and recognize epitopes presented by the CD1d molecule. In the context of the present invention, NKT cells can belong to either the type 1 (invariant) or the type 2 subset.

The "CD1d molecule" refers to a non-MHC derived molecule made of 3 alpha chains and an anti-parallel set of beta chains arranged into a deep hydrophobic groove opened on both sides and capable of presenting lipids, glycolipids or hydrophobic peptides to NKT cells.

The term "CD1d binding motif" refers to an aminoacid sequence which corresponds to the general aminoacid motif [FW]-XX-[ILMV]-XX-[FW], in which F stands for phenylalanine, W for tryptophan, I for isoleucine, L for leucine, M for methionine and V for valine. X represents any aminoacid. In some cases, [FW] in position 7 is replaced by T (for threonine) or H (for histidine).

The term "putative CD1d binding motif" when used herein refers to an aminoacid sequence which corresponds to the general aminoacid motif [FWHY]-$X_2X_3$-[ILMV] or [ILMV]-$X_2X_3$-[FWHY] wherein Y stands for tyrosine. In some cases, the putative motif may be [FWHY]-$X_2$-[ILMV] or [ILMV]-$X_2$-[FWHY] or [FWHY]-$X_2X_3X_4$-[ILMV] or [ILMV]-$X_2X_3X_4$-[FWHY].

The term "immune disorders" or "immune diseases" refers to diseases wherein a reaction of the immune system is responsible for or sustains a malfunction or non-physiological situation in an organism. Immune disorders in the context of the present invention refer to pathology induced by infectious agents and tumor surveillance.

The term "subject" refers to mammals including primates and non-primates.

DETAILED DESCRIPTION OF THE INVENTION

The present invention provides ways to suppress or eliminate, in a subject, an infection with an intracellular pathogen or a tumor, or to increase the immunogenicity of antigens such as some infectious agents and allergens used for vaccination strategies.

In particular, the invention provides ways to increase the expansion and functional activity of CD4+ NKT cells. Such cells are usually classified into two distinct subsets, namely type 1 for NKT cells carrying an invariant TCR alpha chain (Valpha14 in the mouse, Valpha24 in humans), or type 2 NKT cells which present with a diverse alpha chain repertoire. However, recent evidence has suggested that alternative subsets of NKT cells which do not fit in the type 1 or type 2 category. It is the purpose of the present invention to include these non conventional NKT cells, provided they carry the CD4 co-receptor. Upon presentation of an antigen bound to CD1d, NKT cells are rapidly activated, acquire cytolytic properties and secrete a number of cytokines thought to be determinant in influencing other cells from both the innate and adaptive immune systems.

In the context of the present invention, we made the unexpected observation that peptides can be presented by the CD1d molecule and can activate NKT cells recognizing the complex made between CD1d and the peptide. A characteristic of the CD1d molecule is that it is made of two anti-parallel alpha chains forming a cleft sitting atop of a platform made of two anti-parallel beta chains. The cleft is narrow and deep and accept only hydrophobic residues, classically deemed to be only lipids.

The cleft can accommodate a sequence of 7 aminoacids characterized as a hydrophobic residue in position (P) 1 and 7, and an aliphatic residue in P4. P1 is obligatory a hydrophbic residue, such as F, W, H or Y. However, P7 is permissive and can contain alternative residues provided they are not polar. Residues in P4 are preferably aliphatic but this is optional. A general sequence for a CD1d binding motif is therefore [FWTHY]-$X_2X_3$-[ILMV]-$X_5X_6$-[FWTHY]. It should however be clear for those skilled in the art that the motif is symmetrical and that P7 can be considered as P1, and P1 can be considered as P7. The general sequence of a CD1d binding motif is provided here as a general indication without any limiting intention. Peptides and polypeptides of the invention are defined according to their capacity to activate NKT cells by presentation into CD1d molecule.

Many peptides or polypeptides do not naturally carry a CD1d binding motif. However, the present invention also covers peptides or polypeptides which already carry at least one CD1d motif in their natural sequence, as it may be found advantageous to increase the number of said motifs to increase suppression of infections with intracellular pathogens or tumor cells, or to increase immunogenicity to antigens from infectious agents or from allergens.

The present invention relates to the production of peptides or polypeptides which are modified by generating at least one new CD1d binding motif within the natural sequence of said peptides or polypeptides, or by adding at least one CD1d binding motif to said peptide or polypeptide, regardless of the fact that they already carry such a motif.

In a further aspect, the invention also covers the use of at least one isolated hydrophobic peptide or polypeptide comprising at least one CD1d binding motif represented by the general [FW]-$X_2X_3$-[ILMV]-$X_5X_6$-[FWTHY] sequence motif for increasing in a subject elimination of cells infected with intracellular pathogens or tumor cells, or for increasing in said subject the immunogenicity of infectious antigens or allergens used for vaccination.

In yet a further aspect, the invention also covers the use of at least one isolated peptide or polypeptide wherein at least one CD1d binding motif represented by the [FW]-$X_2X_3$-[ILMV]-$X_5X_6$-[FWTHY] sequence has been generated within the natural sequence of said peptide or polypeptide, or has been added to said natural sequence for activating in a subject NKT cells.

In yet a further aspect, the invention also covers the use of at least one isolated hydrophobic peptide or polypeptide comprising at least one new CD1d binding motif represented by the [FW]-$X_2X_3$-[ILMV]-$X_5X_6$-[FWTHY] sequence as a medicament for suppressing in a subject infection with intracellular pathogens or tumor cells, or to increase the efficiency of antigens from infectious agents or from allergens for vaccination.

A further advantage of the present invention is that addition of aromatic aminoacid residues in peptides or polypeptides creates CD1d binding motifs which are promiscuous in the sense that said motifs can bind to CD1d molecules of all or of a very large majority of subjects. This is due to the fact that the CD1d molecule itself presents a very limited degree of polymorphism. As in addition the polymorphism of NKT cell antigenic receptor is highly restricted, it should be obvious for the one skilled in the art that the same aromatic aminoacid addition is applicable to all subjects considered for application of the present invention.

This is in sharp contrast with peptide or polypeptide motifs binding to major histocompatibility class II molecules, wherein a large number of peptides can be delineated which contain the appropriate sequence. This is due to the minimum constraints imposed to MHC class II binding peptides and to the large polymorphism of class II molecules.

Peptides and polypeptides which are the object of the present invention are obtained as follows:
(1) a peptide or polypeptide is, optionally, evaluated for its capacity to activate NKT cells. This is carried out by incubating said peptide or polypeptide with a cell line expressing the CD1d molecule. Examples of such cell lines are known in the art (for instance JAWS2 cells). In a preferred embodiment, the cell line is not presenting MHC class II molecules and is transduced for hyperexpression of CD1d using a viral vector containing the DNA sequence of CD1d or any other means known in the art to introduce a gene in a cell. Methods for cell transduction are known in the art. The cell line is loaded in culture with the peptide or polypeptide. Efficient presentation of the peptide or polypeptide by the CD1d molecule is then evaluated by measuring the activation of NKT cells. Such cells can be obtained from peripheral blood by, for instance, magnetic sorting and maintained in culture with stimulants such as alpha-gal-ceramide, in the presence of cytokines such as IL-2 and IL-15 or IL-7. These methods are described in the art (see for instance Brutkiewicz Journal of Immunology 2006, 177: 769-775). Activation of NKT cells is assessed using methods such as evaluation of cytokine production. Peptides or polypeptides which show no or only limited activation of NKT cells are selected.

(2) the peptide or polypeptide aminoacid sequence is then evaluated for the presence of at least one motif corresponding to the [FWHY]-$X_2X_3$-[ILMV] or [ILMV]-$X_2X_3$-[FWHY] sequence (putative CD1d binding motif) using algorithms well known in the art such as expasy.org/tools/scanprosite/

More particularly, said algorithms allow the prediction within a peptide or polypeptide of one or more 7 aminoacid-long sequences which correspond to the [FWHY]-$X_2X_3$-[ILMV]-$XX_6$-[FWHY] sequence and thereby has the potential to fit into the cleft of a CD1d molecule. More particularly, said algorithms allow the prediction of aminoacid sequences corresponding to [FW]-$X_2X_3$-[ILMV] or to [ILMV]-$X_2X_3$-[FW].

(3) sequences of aminoacids identified by said algorithms are examined and modified by aminoacid substitution to increase the potential to bind to CD1d. This essentially includes the substitution of aminoacids in position P1 by a hydrophobic residue such as F, W, H or Y and/or substitution of aminoacids in position P7 by F, W, T, H or Y, when required.

(4) optionally, a putative CD1d binding motif is identified which corresponds to [FWHY]-$X_2$-[ILMV] or [ILMV]-$X_2$-[FWHY], or [FWHY]-$X_2X_3X_4$-[ILMV] or [ILMV]-$X_2X_3X_4$-[FWHY]. In such cases addition of an $X_3$ or deletion of $X_4$, respectively, is found advantageous to reconstitute a CD1d binding motif which comprises an aliphatic aminoacid residue in position P4. More generally, the putative CD1d binding motif could correspond to the general formula [FWHY]-R-[ILMV] or [ILMV]-R-[FWHY] wherein R represents an aminoacid or an aminoacid sequence.

(5) optionally, a CD1d motif can be added to the aminoacid sequence of the peptide or polypeptide, either in carboxy-terminal or amino-terminal end of the sequence, or anywhere within the peptide or polypeptide natural sequence (6) optionally, peptides or polypeptides of the invention can be modified by generating at least one CD1d motif and by addition of at least one CD1d binding motif.

(7) optionally, the synthetic peptide encompassing the sequence containing a CD1d binding motif is tested in vitro using a cell line expressing the CD1d molecule as described in (1).

(8) optionally, the capacity of the peptide or polypeptide modified by substitution, addition or deletion of aminoacids as described above to bind to CD1d is tested in vitro using tetramers of the CD1d molecule to detect NKT cells specific for such peptide. One possibility is to use fluorescence-labeled tetramers and detection using fluorescence activated cell sorting (facs).

It should be clear for the one skilled in the art that substitution or addition of aminoacid residues, or addition of CD1d binding motif(s) can be carried out using a non-physiological aminoacid residues such as D-aminoacids or an organic compound.

The peptide or polypeptide containing the aminoacid substitution, addition or deletion is then produced using methods known in the art for the production of recombinant proteins using expression systems such as bacterial cells, yeast cells, insect cells, plant cells or mammalian cells.

According to the present invention medicaments are envisaged for the treatment of diseases due to intracellular pathogens. Examples of said intracellular pathogens include ssDNA, dsDNA and RNA viruses, bacteria and mycobacteria, and parasites.

Medicaments are also envisaged for the treatment of tumors.

Further, medicaments are also envisaged for vaccination strategies towards infectious agents with primarily extracellular life cycle and towards allergens.

It should be understood that any of the peptides or polypeptides envisaged in the context of the present invention may be administered in the form of gene for transgenesis, which may be carried out using viral vectors or other means known by those skilled in the art. In such a case, it may be found advantageous to alter the aminoacid sequence of the viral vector itself by adding a CD1d binding motif, thereby increasing expression of the transgene.

In a preferred embodiment, the peptide can be constituted of a CD1d binding motif encompassing the [FW]-$X_2X_3$-[ILMV]-$X_5X_6$-[FWTHY] sequence. Yet in more preferred embodiment, the said peptide also contains aminoacid flanking residues at either the aminoterminal or carboxyterminal end, or at both ends of said peptide. In yet a preferred embodiment, said peptide contains bulky aminoacid residues in flanking residues. In yet another embodiment, said peptide carries at least one class II restricted T cell epitope. In yet another embodiment, said peptide contains aminoacid flanking residues which are part of the natural sequence from which the peptide is derived.

The medicament of the invention is usually, though not necessarily, a (pharmaceutical) formulation comprising as active ingredient at least one of the peptides or polypeptides of the invention or a gene therapeutic vector capable of expressing said peptides or polypeptides. Apart from the active ingredient(s), such formulation will comprise at least one of a (pharmaceutically acceptable) diluent.

In general, administration of peptides or polypeptides of the invention increases activation of the innate immune system, more particularly activation of NKT cells, more particularly the production of cytokines associated with NKT cell activation, more particularly the cytolytic properties of NKT cells.

The route of administration for peptides or polypeptides of the present invention may vary according to the indication and/or the nature of the peptides or polypeptides. Examples are subcutaneous or intramuscular injection of vaccines for infectious disease and for allergens or for tumors, or oral, nasal or intratracheal administration for infections with intracellular pathogens. The present invention intends to cover all other possible routes of administration such as intranasal, sublingual, percutaneous, intramuscular, intrarectal or intravaginal.

As explained in detail further on, the peptides or polypeptides of the present invention can be made by chemical synthesis, which allows the incorporation of non-natural amino acids.

Another aspect of the present invention relates to methods to obtain peptides or polypeptides comprising an artificial sequence able to activate NKT cells, said method comprising the steps of:
(a) identification of peptides or polypeptides which do not, or only to a limited extend, activate NKT cells;
(b) introduction of at least one CD1d binding motif by aminoacid addition, substitution and/or deletion.

Such methods include the identification of epitopes which can be modified to carry a CD1d binding motif by aminoacid substitution, addition or deletion. Ways for in silico identification of putative NKT-cell epitopes are amply known in the art and some aspects are elaborated upon hereafter.

For instance, when said putative NKT-cell epitope is identified, synthetic peptides encompassing said sequence are produced. Alternative peptides are also synthesized which include the aminoacid substitution, addition or deletion judged to be appropriate to increase the capacity of the aminoacid sequence to bind to CD1d. The peptide encompassing the natural sequence and peptides with aminoacid substitution(s), additions, deletions or combinations of these are tested for their capacity to bind CD1d tetramers and/or to activate NKT cells by loading antigen-presenting cells expressing CD1d.

For instance, soluble CD1d molecules are obtained and made tetrameric by synthesis and/or chemical coupling. The CD1d molecule is purified by affinity chromatography. Soluble CD1d molecules are incubated with a biotin-labeled reference peptide produced according to its strong binding affinity for said CD1d molecule. Peptides to be assessed for CD1d binding are then incubated at different concentrations and their capacity to displace the reference peptide from its CD1d binding is calculated by addition of neutravidin. Methods can be found in for instance Texier et al., (2000) J. Immunology 164, 3177-3184) for peptides presented by the major histocompatibility class II molecule, but the method can easily be applied to CD1d-restricted T cell epitopes.

Optionally, the binding of the peptides of the invention to CD1d tetramers can be evaluated by incubation with NKT cells and fluorescence-activated cell sorting (facs) analysis. These methods are well described in the art.

Alternatively, antigen-presenting cells such as JAWS2 cells which express CD1d but do not express major histocompatibility class II complexes are loaded with the peptides or polypeptides of the invention and their capacity to activate NKT cells is evaluated by the proliferation of NKT cells as assessed by incorporation of tritiated thymidine. These methods are well known by the one skilled in the art. The peptides or polypeptides of the invention have a mean NKT cell stimulation index of greater than or equal to 2. A peptide having a NKT cell stimulation index of greater than or equal to 2 is considered useful as a candidate to carry out the present invention.

Aminoacid substitution(s) identified as suitable for the present invention, addition or deletion of said aminoacids are then introduced into full-length peptide or polypeptide for practicing the invention.

The peptides or polypeptides of the invention can be produced by recombinant expression in, e.g., bacterial cells (e.g. *Escherichia coli*), yeast cells (e.g., *Pichia* species, *Hansenula species, Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques. Recombinantly produced peptides or polypeptides of the invention can be derived from a larger precursor protein, e.g., via enzymatic cleavage of enzyme cleavage sites inserted adjacent to the N- and/or C-terminus of the peptide or polypeptide, followed by suitable purification.

In view of the limited length of some of the peptides or polypeptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205. This provides the potential to achieve protein synthesis which is beyond the scope of SPPS. Many proteins with the size of 100-300 residues have been synthesized successfully by this method.

The physical and chemical properties of a peptide or polypeptide of interest (e.g. solubility, stability) is examined to determine whether the peptide is/would be suitable for use in therapeutic compositions. Typically this is optimized by adjusting the sequence of the peptide. Optionally, the peptide can be modified after synthesis (chemical modifications e.g. adding/deleting functional groups) using techniques known in the art.

The production of genetically-modified peptides or polypeptides relies on methods well known by those skilled in the art, including cloning, site-directed mutagenesis and growth.

The present invention also relates to nucleic acid sequences encoding the peptides or polypeptides of the invention and methods for their use, e.g., for recombinant expression or in gene therapy. In particular, said nucleic acid sequences are capable of expressing peptides of the invention.

In gene therapy, recombinant nucleic acid molecules encoding the peptides or polypeptides of the present invention can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding a peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for a peptide or polypeptide according to the invention may be used in gene therapy.

The medicament of the invention is usually, but not necessarily, a (pharmaceutical) formulation comprising as active ingredient at least one of the peptides or polypeptides of the invention, a gene therapeutic vector capable of expressing said peptide or polypeptide. Apart from the active ingredient(s), such formulation will comprise at least one of a (pharmaceutically acceptable) diluent. Typically, pharmaceutically acceptable compounds can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need of a single administration can also vary and will depend on factors such as the physical status of the subject (as for instance weight and age), the status of the condition to be prevented or treated, and the experience of the treating doctor, physician or nurse.

The term "diluents" refers for instance to physiological saline solutions. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Peptides or polypeptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the peptide or polypeptide to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

The present invention will now be illustrated by means of the following examples, which are provided without any limiting intention. Furthermore, all references described herein are explicitly included herein by reference.

EXAMPLES

Example 1

Mycobacteria

*Mycobacterium tuberculosis* is responsible for thousands of deaths every year. The only available vaccination, the Calmette-Guérin *Mycobacterium bovis*-based vaccine (BCG), is not efficient. One candidate for improving vaccination is the 6 kDa early secretory antigen target (ESAT-6) produced by *M. tuberculosis*, which is one of the main antigens recognized both by humans and animals such as mice.

The sequence of ESAT-6 (SEQ ID1) was analyzed using computer algorithms to identify CD1d binding motifs corresponding to the [FW]-$X_2X_3$-[ILMV]-$X_5X_6$-[FWTHY] sequence. None of such motif was found. A mutation A to F and G to F was introduced by standard mutagenesis methods in position 14 and 20, respectively, which generated a CD1d binding motif susceptible to activate NKT cells (mutated ESAT-6; SEQ ID2).

C57BL/6 mice are immunized with ESAT-6 (SEQ ID1) or mutated ESAT-6 of SEQ ID NO:2 together with an adjuvant such as alum. Four injections of 50 μg of the peptide are made at fortnight intervals. Two weeks after the last immunization, mice are sacrificed and CD4+ T lymphocytes prepared from the spleen by a combination of density gradient centrifugation and selection on antibody-coated magnetic beads.

CD4+ T cells are then activated and expanded in vitro using JAWS2 cells as antigen-presenting cells loaded with mutated ESAT-6 of SEQ ID2. JAWS2 cells do not express major histocompatibility class II determinants, preventing thereby activation of class II restricted CD4+ T cells, but JAWS2 cells express CD1d and can therefore be used to assay the capacity of peptides to activate NKT cells. It is observed that only NKT cells obtained from mice immunized with the mutated ESAT-6 (SEQ ID2) are activated by loaded JAWS2 cells, while NKT cells form mice immunized with ESAT-6 (SEQ ID1) are not activated.

To evaluate the cytolytic properties of CD4+ NKT cells activated by mutated ESAT-6 of SEQ ID2, JAWS2 cells were analyzed after 18 h incubation with NKT cells for induction of apoptosis. Thus, annexin V binding to the surface of apoptotic cells is detected by addition of a fluorescence-labeled annexin V. Results indicate that JAWS2 cells incubated with NKT cells obtained from mice immunized with mutated ESAT-6 (SEQ ID2) are induced into apoptosis.

These results therefore show that single aminoacid substitutions generating a CD1d binding motif are sufficient to elicit activation of NKT cells and apoptosis of antigen-presenting cells.

Example 2

EG7 Tumor

EG7 tumor cells (H-2b) are derived from a thymoma transduced with an ovalbumin(ova)-containing construct. A CD1d restricted ova epitope is presented by such cells, but this is known to be insufficient to trigger NKT activation and tumor cell killing (Castano et al, Science 1995, 269: 223-226).

A search was made using computer algorithms to identify alternative epitopes which could be altered by aminoacid substitution to generate new CD1d binding motifs. Two sequences were identified in position 16-22 (FKELKVH, SEQ ID NO: 9) and 181-187 (FKGLWEK, SEQ ID NO: 10). H22 and K187 were mutated to F in the ova sequence thereby generating a protein of SEQ ID4.

Immunization of mice with ova of SEQ ID4 was carried out using 50.1 g of ova in alum administered subcutaneously on 4 occasions separated by an interval of 10 days. A control group was immunized with ova in natural sequence (SEQ ID3). All mice were then engrafted with $10^6$ EG7 tumor cells injected in the flank and the growth of the tumor was followed over time. Mice preimmunized with ova of SEQ ID4 rejected the tumor while control mice preimmunized with ova in natural SEQ ID3 did not.

In vitro killing of EG7 cells was evaluated using NKT cells prepared from the spleen using magnetic bead sorting. The NKT cells were first stimulated for 4 h in vitro with antigen-presenting cells loaded with ova of SEQ ID4. EG7 cells were labeled at membrane level with 1 μM $DiOC_{18}$ (3,3'-dioctadecycloxacarbocyanine perchlorate from Invitrogen). EG7 cells ($1\times10^5$ per well) were then cultured for 18 h at 37° C. in the presence of NKT cells obtained from each one of the 2 mouse groups, using ratios of 1/1 to 1/5 (EG7 cells versus NKT cells). After 18 h, cells were harvested and stained for Annexin V and 7-AAD following manufacturer's instructions (Apoptosis Detection kit; BD Biosciences) and analyzed on a FACSCantoII flow cytometer (BD Biosciences). Results show that EG7 cells incubated with NKT cells obtained from mice immunized with ova of SEQ ID4 are induced into apoptosis, while NKT cells obtained from control mice immunized with ova of SEQ ID3 did not induce a significant degree of tumor cell apoptosis.

Example 3

Influenza

Influenza virus hemagglutinin is a major antigen used for vaccination purposes. The efficacy of vaccination is however limited by the relatively weak immunogenicity of hemagglutinin.

The sequence of hemagglutinin (SEQ ID5) contains 3 sequences that are suitable for mutation to obtain aminoacid sequences encoding a CD1d binding motif of the [FW]-$X_2X_3$-[ILMV]-$X_5X_6$-[FWTHY] format. cDNA of hemagglutinin was obtained and 3 mutations were introduced by standard mutagenesis methods to replace the aminoacid in position 7 of the CD1d binding motif into F (phenylalanine). These mutations corresponded to V314F, A348F and K459F, in which valine, alanine and lysine in position 314, 348 and 459, respectively, were mutated to phenylalanine. Mutated hemagglutinin of SEQ ID6 was produced by recombinant technology.

Mice were immunized 4 times with either hemagglutinin of SEQ ID5 or SEQ ID6 by the subcutaneous route at 1 week intervals. Seven days after the last immunization, mice were sacrificed and CD4+ T cells were prepared from the spleen using magnetic bead sorting. JAWS2 cells were loaded with mutated hemagglutinin of SEQ ID6 by incubation for 18 h at room temperature. The cells were then washed and incubated in the presence of CD4+ T cells obtained from mice immunized with either hemagglutinin of SEQ ID5 or hemagglutinin of SEQ ID6. It is observed that a significant proportion of NKT cells are activated when obtained from mice immunized with hemagglutinin of SEQ ID6 but not with hemagglutinin of SEQ ID5, demonstrating that immunization with hemagglutinin of SEQ ID6 had induced an expansion of NKT cells in vivo.

Further, mutated hemagglutinin of SEQ ID6 is used for vaccination. It is observed that mice immunized with hemagglutinin of SEQ ID6 produce higher concentrations of hemagglutinin specific antibodies.

Example 4

Allergen

Vaccination for allergic diseases is currently limited by the relative weak immunogenicity of allergens. Methods by which an increased production of allergen-specific IgG antibodies could be obtained are highly desirable.

Der p 2 is one of the major allergens from house dust mite, *D. pteronyssinus*, associated with allergic rhinitis and asthma throughout the world. A search within the sequence of Der p 2 using computer algorithms identified no sequence which carried a CD1d binding motif. A motif made of 7 aminoacids (FAALAAF, SEQ ID NO: 11) was added at the carboxyterminal end of the sequence of Der p 2. Such a sequence encodes a CD1d binding motif corresponding to the sequence [FW]-$X_2X_3$-[ILMV]-$X_5X_6$-[FWTHY]. To note, a major T cell epitope presented by major histocompatibility class II complexes is known to be located in position 24-35 of the mature Der p 2 molecule.

Two groups of C57BL/6 mice (H-2b) were immunized with either native Der p 2 (SEQ ID7) or native Der p 2 wherein a CD1d binding motif had been added (SEQ ID8), using 50 μg of protein in alum injected subcutaneously 4 times at 10 days intervals. Mice were then bled and the concentration of specific anti-Der p 2 antibodies was tested by direct binding ELISA. It is observed that the concentration of antibodies is 10-fold higher in the group of mice immunized with Der p 2 of SEQ ID8.

Further, CD4+ T cells were prepared from the spleen of each mouse from the 2 groups, using magnetic bead sorting. Such cells ($10^6$ cells/well) were cultured with dendritic cells prepared from syngeneic CD1d KO mice. Such cells can only activate class II restricted CD4+ T cells. It is observed that cells obtained from mice immunized with Der p 2 of SEQ ID8 proliferate with a stimulation index 4-fold higher than cells obtained from mice immunized with native Der p 2 (SEQ ID7).

It is therefore concluded that the presence of a CD1d binding motif increases the production of specific antibodies and the proliferation of class II restricted CD4+ T cells.

It should be understood that the examples provided here are not exhaustive and that combinations of proteins or peptides containing various numbers of aminoacid substitutions or deletions to generate new CD1d binding motifs or containing various numbers of added CD1d binding motifs are envisioned within the scope of the present invention.

The invention claimed is:

1. A method of treating in a mammalian subject an infection, the method comprising
identifying a peptide or polypeptide from an agent causing the infection in the mammalian subject, wherein the peptide or polypeptide does not activate NKT cells when the peptide or polypeptide is incubated with a cell line expressing CD1d and NKT cells;
introducing at least one, or at least one additional, CD1d binding motif comprising [FWHY]-$X_2X_3$-[ILMV]-$X_5X_6$-[FWHY] into the said peptide or polypeptide so as to generate a modified peptide or polypeptide;
selecting a modified peptide or polypeptide that activates NKT cells when the peptide or polypeptide is incubated with a cell line expressing CD1d and NKT cells; and administering the modified peptide or polypeptide that activates NKT cells to the mammalian subject, wherein identifying a peptide or polypeptide that does not activate NKT cells comprises determining the capacity of the peptide or polypeptide to bind to CD1d, and, for peptides or polypeptides having the capacity to bind to CD1d, determining the ability to activate NKT cells by incubation of the modified peptide or polypeptide with cells expressing CD1d, followed by addition of a population of NKT cells, and detecting NKT cell activation.

2. A method of activating NKT cells in a mammal, the method comprising identifying a peptide or polypeptide that does not activate NKT cells when the peptide or polypeptide is incubated with a cell line expressing CD1d and NKT cells;

introducing at least one, or at least one additional, CD1d binding motif comprising [FWHY]-$X_2X_3$-[ILMV]-$X_5X_6$-[FWHY] into the peptide or polypeptide so as to generate a modified peptide or polypeptide;

selecting a modified peptide or polypeptide that activates NKT cells; and administering the said modified peptide or polypeptide that activates NKT cells to the mammal, wherein the NKT cells are Type I NKT cells, wherein identifying a peptide or polypeptide that does not activate NKT cells comprises determining the capacity of the peptide or polypeptide to bind to CD1d, and, for peptides or polypeptides having the capacity to bind to CD1d, determining the ability to activate NKT cells by incubation of the modified peptide or polypeptide with cells expressing CD1d, followed by addition of a population of NKT cells, and detecting NKT cell activation.

3. The method of claim 1, further comprising selecting a modified peptide or polypeptide that activates cytolytic activity and cytokine production by CD4+ NKT cells in the mammalian subject.

4. The method of claim 2, further comprising selecting a modified peptide or polypeptide that activates a cytolytic activity and cytokine production by CD4+ NKT cells in the mammalian subject.

5. The method of claim 1, wherein selecting a modified peptide or polypeptide that activates NKT cells comprises determining the capacity of the peptide or polypeptide to bind to CD1d, and, for peptides or polypeptides having the capacity to bind to CD1d, determining the ability to activate NKT cells by incubation of the modified peptide or polypeptide with cells expressing CD1d, followed by addition of a population of NKT cells, and detecting NKT cell activation.

6. The method of claim 2, wherein selecting a modified peptide or polypeptide that activates NKT cells comprises determining the capacity of the peptide or polypeptide to bind to CD1d, and, for peptides or polypeptides having the capacity to bind to CD1d, determining the ability to activate NKT cells by incubation of the modified peptide or polypeptide with cells expressing CD1d, followed by addition of a population of NKT cells, and detecting NKT cell activation.

7. A method of treating a tumor in a mammalian subject, the method comprising identifying a peptide or polypeptide from the tumor, in the mammalian subject, wherein the peptide or polypeptide does not activate NKT cells when the peptide or polypeptide is incubated with a cell line expressing CD1d and NKT cells;

introducing at least one, or at least one additional, CD1d binding motif comprising [FWHY]-$X_2X_3$-[ILMV]-$X_5X_6$-[FWHY] into the said peptide or polypeptide so as to generate a modified peptide or polypeptide;

selecting a modified peptide or polypeptide that activates NKT cells when the peptide or polypeptide is incubated with a cell line expressing CD1d and NKT cells, and that activates cytolytic activity and cytokine production by CD4+ NKT cells when administered to a mammalian subject;

administering the modified peptide or polypeptide to the mammalian subject in need of treatment;

wherein identifying a peptide or polypeptide that does not activate NKT cells comprises determining the capacity of the peptide or polypeptide to bind to CD1d, and, for peptides or polypeptides having the capacity to bind to CD1d, determining the ability to activate NKT cells by incubation of the modified peptide or polypeptide with cells expressing CD1d, followed by addition of a population of NKT cells, and detecting NKT cell activation.

8. The method of claim 7, wherein selecting a modified peptide or polypeptide that activates NKT cells comprises determining the capacity of the peptide or polypeptide to bind to CD1d, and, for peptides or polypeptides having the capacity to bind to CD1d, determining the ability to activate NKT cells by incubation of the modified peptide or polypeptide with cells expressing CD1d, followed by addition of a population of NKT cells, and detecting NKT cell activation.

* * * * *